US012354748B2

(12) United States Patent
Mei et al.

(10) Patent No.: US 12,354,748 B2
(45) Date of Patent: Jul. 8, 2025

(54) HEALTH CONDITION EVALUATION BASED ON TEMPORAL ANALYSIS OF DIETARY HABITS

(71) Applicant: International Business Machines Corporation, Armonk, NY (US)

(72) Inventors: Lijun Mei, Beijing (CN); Jie Ma, Nanjing (CN); Xin Zhou, Beijing (CN); Qi Cheng Li, Beijing (CN); Hao Chen, Chaoyang District (CN)

(73) Assignee: International Business Machines Corporation, Armonk, NY (US)

( * ) Notice: Subject to any disclaimer, the term of this patent is extended or adjusted under 35 U.S.C. 154(b) by 1022 days.

(21) Appl. No.: 16/991,020

(22) Filed: Aug. 12, 2020

(65) Prior Publication Data

US 2022/0051793 A1   Feb. 17, 2022

(51) Int. Cl.
| | | |
|---|---|---|
| *G16H 50/20* | (2018.01) | |
| *G16H 10/60* | (2018.01) | |
| *G16H 20/60* | (2018.01) | |
| *G16H 50/30* | (2018.01) | |
| *G16H 50/70* | (2018.01) | |

(52) U.S. Cl.
CPC ............. *G16H 50/20* (2018.01); *G16H 10/60* (2018.01); *G16H 20/60* (2018.01); *G16H 50/30* (2018.01); *G16H 50/70* (2018.01)

(58) Field of Classification Search
USPC .......................................................... 702/19
See application file for complete search history.

(56) References Cited

U.S. PATENT DOCUMENTS

| | | |
|---|---|---|
| 2014/0255882 A1 | 9/2014 | Hadad |
| 2015/0289809 A1 | 10/2015 | Pacione |
| 2017/0147775 A1 | 5/2017 | Ohnemus |
| 2017/0220772 A1 | 8/2017 | Vleugels |
| 2021/0151188 A1* | 5/2021 | Bergh ............... A61B 5/486 |

FOREIGN PATENT DOCUMENTS

WO        2019183404 A1    9/2019

OTHER PUBLICATIONS

Batis, Carolina, et al. "Longitudinal analysis of dietary patterns in Chinese adults from 1991 to 2009." British Journal of Nutrition 111.8 (2014): 1441-1451.*
Mell et al., "The NIST Definition of Cloud Computing", National Institute of Standards and Technology, Special Publication 800-145, Sep. 2011, 7 pages.
Thomaz, et al., "Inferring Meal Eating Activities in Real World Settings from Ambient Sounds: A Feasibility Study", IUI 2015 • Affect/Health, Mar. 29-Apr. 1, 2015, pp. 427-431, <https://dl.acm.org/citation.cfm?id=2701405>.

* cited by examiner

*Primary Examiner* — G. Steven Vanni
(74) *Attorney, Agent, or Firm* — Caleb D. Wilkes

(57) ABSTRACT

Evaluation of a health condition includes obtaining a correlation between dietary habits and health issues of a plurality of reference users. The correlation is determined based on reference patterns. Each of the reference patterns indicates temporal characteristics of at least one dietary habit and at least one health issue of a reference user of the plurality of reference users. A target pattern of a target user is determined at least in part based on a profile for the target user. The target pattern at least indicates temporal characteristics of at least one dietary habit of the target user. An evaluation of a health condition of the target user is generated based on the target pattern and the correlation.

17 Claims, 9 Drawing Sheets

HEALTH CONDITION EVALUATION BASED ON TEMPORAL ANALYSIS OF DIETARY HABITS

BACKGROUND

The present disclosure generally relates to the field of health conditions evaluation, and more specifically, to a method, system, and computer program product for evaluating health conditions based on the analysis of temporal relations between dietary habits and health conditions of a plurality of users.

Certain dietary habits can be the root cause of specific health issues. The relationship between dietary habits and health conditions is usually determined based on experience and/or extensive research. Due to the complexity of dietary structures and individual differences, it can be challenging to directly and precisely determine a correlation between dietary habits and health issues.

SUMMARY

According to one embodiment of the present disclosure, there is provided a computer-implemented method. A correlation between dietary habits and health issues of a plurality of reference users is obtained. The correlation is determined based on the reference patterns, each of which indicates temporal characteristics of at least one dietary habit and at least one health issue of a reference user of the plurality of reference users. For a target user, his/her target pattern is determined at least in part based on a profile of the target user. The target pattern at least indicates temporal characteristics of at least one dietary habit of the target user. Based on the target pattern and the correlation, an evaluation of a health condition of the target user is generated.

According to another embodiment of the present disclosure, there is provided a system. The system includes a processing unit and a memory coupled to the processing unit. The memory stores instructions that, when executed by the processing unit, perform actions. The actions include obtaining a correlation between dietary habits and health issues of a plurality of reference users. The correlation is determined based on reference patterns, each of which indicates temporal characteristics of at least one dietary habit and at least one health issue of a reference user of the plurality of reference users. The actions also include determining a target pattern of a target user at least in part based on a profile of the target user. The target pattern at least indicates temporal characteristics of at least one dietary habit of the target user. The actions further include generating an evaluation of a health condition of the target user based on the target pattern and the correlation.

According to yet another embodiment of the present disclosure, there is provided a computer program product. The computer program product is tangibly stored on non-transient machine-readable medium and includes machine-executable instructions. The machine-executable instructions, when executed on a device, cause the device to perform actions. The actions include obtaining a correlation between dietary habits and health issues of a plurality of reference users. The correlation is determined based on reference patterns, each of which indicates temporal characteristics of at least one dietary habit and at least one health issue of a reference user of the plurality of reference users. The actions also include determining a target pattern of a target user at least in part based on a profile of the target user. The target pattern at least indicates temporal characteristics of at least one dietary habit of the target user. The actions further include generating an evaluation of a health condition of the target user based on the target pattern and the correlation.

BRIEF DESCRIPTION OF THE DRAWINGS

The following detailed description, given by way of example and not intended to limit the invention solely thereto, will best be appreciated in conjunction with the accompanying drawings, in which.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Figure 1:
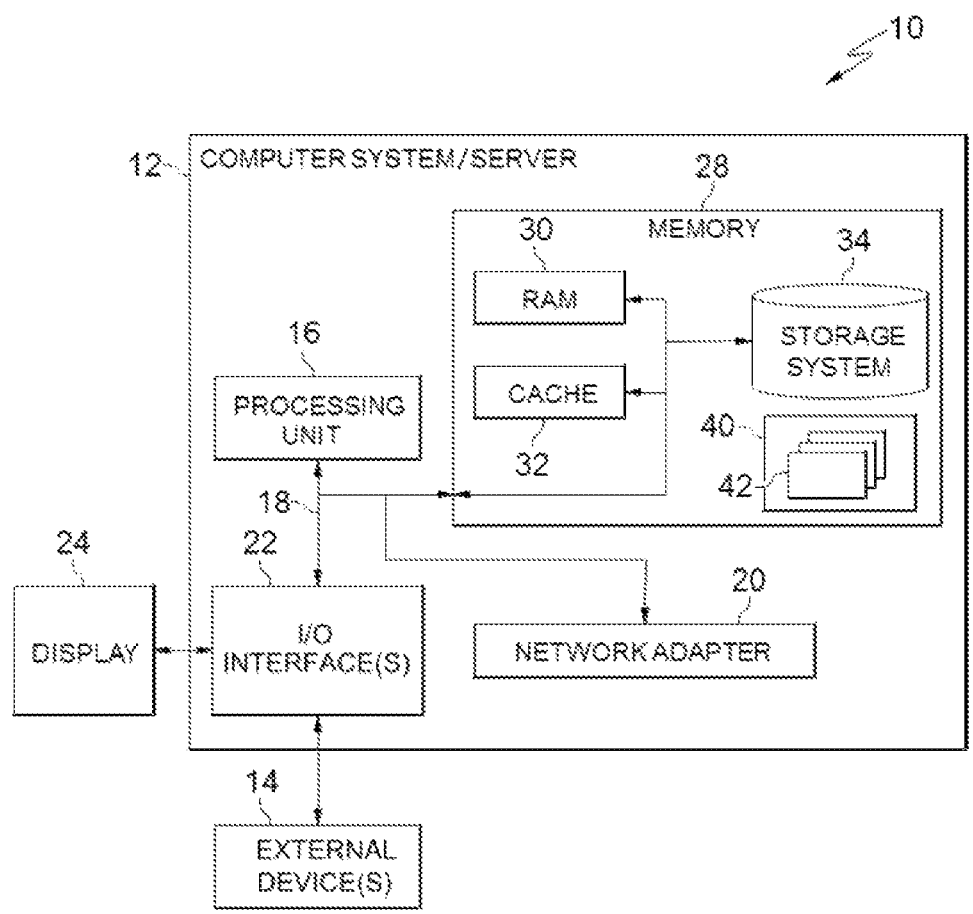
FIG. 1 depicts a cloud computing node, according to an embodiment of the present disclosure.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12 or a portable electronic device such as a communication device, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA)

bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
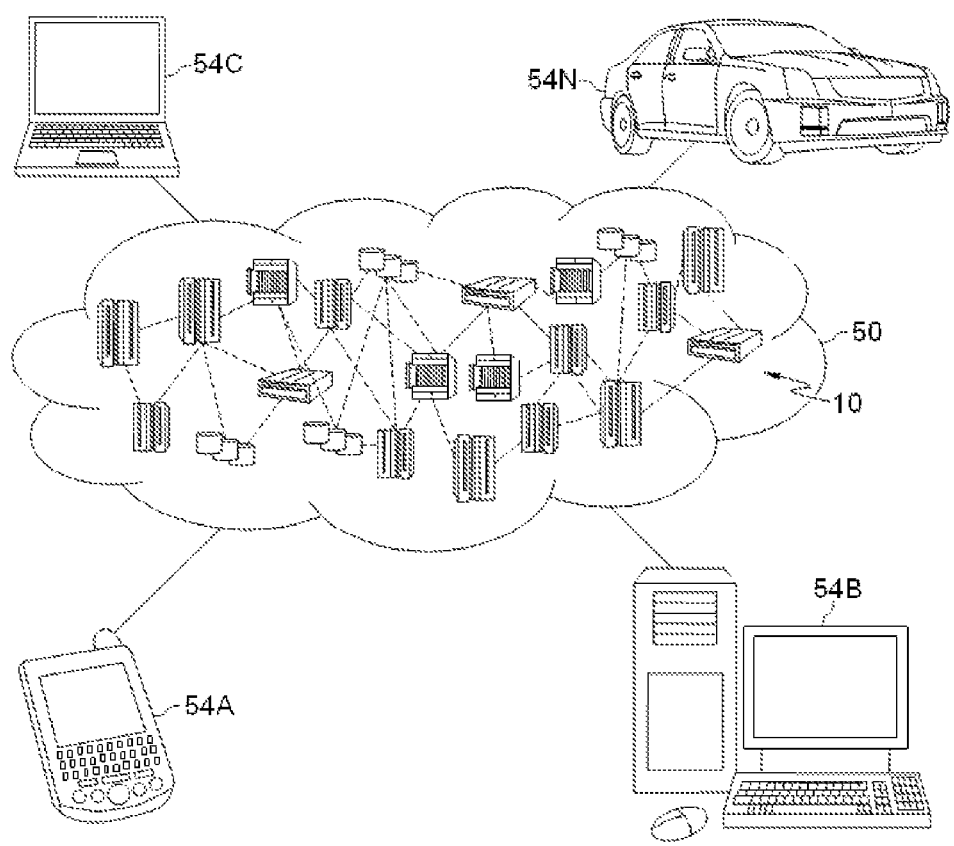
FIG. 2 depicts a cloud computing environment, according to an embodiment of the present disclosure.

Referring now to FIG. 2, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
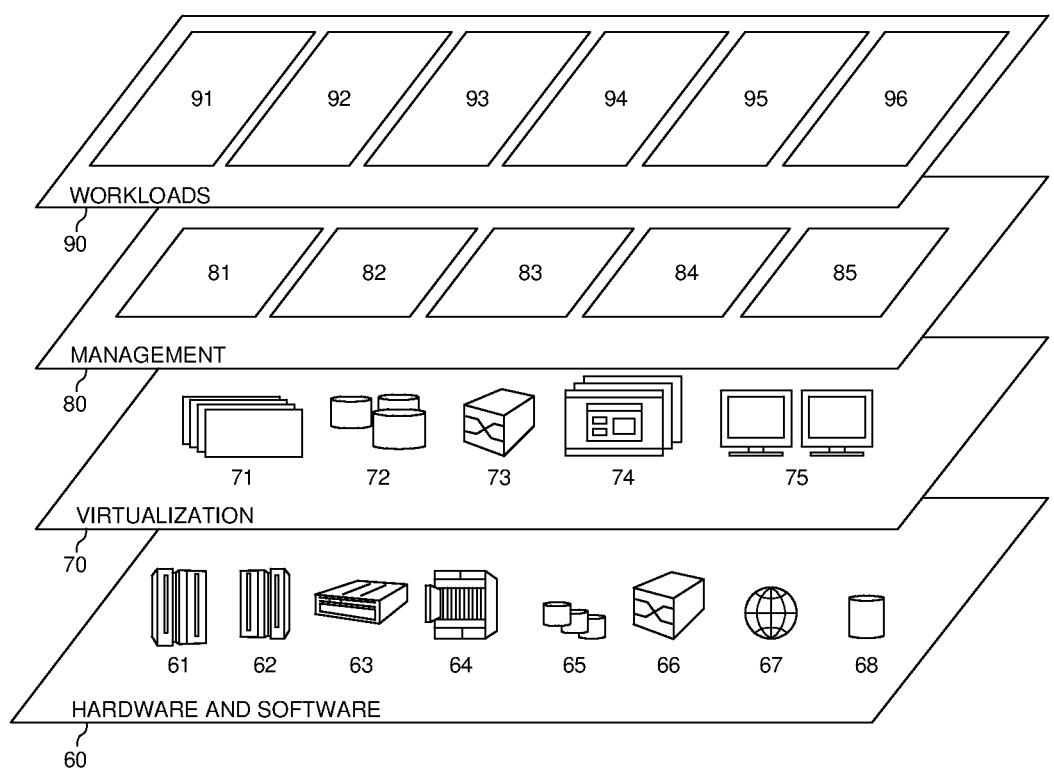
FIG. 3 depicts abstraction model layers, according to an embodiment of the present disclosure.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and health condition evaluation 96.

As used herein, the term "dietary habit" refers to a preference for and/or an actual intake of different kinds of foods and drinks. The term "dietary habit" further refers to regularity regarding how meals are taken, for example, eating breakfast, lunch, and dinner regularly or irregularly. Examples of dietary habits include, but are not limited to, excessive food consumption, increase intake of salty and/or spicy food, dependence on carbonated drinks, and the like. As used herein, the term "health issue" refers to a disease associated with a user and/or uncomfortable feeling perceived by the user.

As mentioned above, dietary habits can be responsible for certain health issues. A healthy diet is an important factor for good health. For example, excessive food intake can lead to over nutrition, which may cause conditions such as obesity, kidney or gallbladder stones, high blood pressure, hyperlipidemia, and other diseases. Long-term inadequate nutritional intake can also cause health problems such as anemia, lack of important nutrients, and vitamin deficiencies. Thus, a poor (unhealthy) diet can negatively affect people's health and cognitive behavior, and even cause life-threatening situations.

Moreover, some dietary preferences and/or situations may increase the risk of foodborne diseases including, for example, eating raw food, eating food prepared without proper hygiene, and/or drinking water for unknown sources. Additionally, people with pre-existing conditions such as diabetes, heart disease, kidney disease, etc., need to be particularly careful with their diets (e.g., follow low sugar and/or low fat diets).

Accordingly, it is important to monitor dietary habits and their correlation with certain health conditions. Currently, relationships between dietary habits and health issues are determined based merely on experience and extensive research. Due to the complexity of dietary structures and individual differences, health issues cannot be effectively and efficiently predicted from dietary habits. Some model-based approaches are proposed to predict health issues and/or evaluate health conditions. However, those models are derived from general data mining and statistics without taking the specific characteristics of individual users into account. That is, those known approaches are not personalized, and thus are not accurate in many situations.

In order to, at least partially, solve the above and other potential problems, embodiments of the present disclosure provide an innovative approach to evaluation of health conditions based on a correlation between different health issues and dietary habits determined using reference patterns of reference users. Each reference pattern indicates temporal characteristics of at least one dietary habit and at least one health issue of a respective reference user. For example, a temporal characteristic of a dietary habit may include a time period during which a user has the dietary habit, or a point in time at which the dietary habit occurs. Therefore, the determined correlation may correlate the dietary habits and health issues based on relations in the temporal dimension.

For a given target user, his/her target pattern can be determined at least in part based on the profile of the target user. The profile of the target user may include information on at least one dietary habit of the target user. A health condition of the target user can then be evaluated based on the target pattern and the determined correlation.

It will be appreciated from the following description that, according to embodiments of the present invention, a health condition of a target user can be evaluated based on the collected dietary habits of the target user. In making the evaluation, the correlation between dietary habits and health issues is also taken into account, and such correlation is determined based on the dietary habits and health issues of multiple reference users. In this way, a prediction associated with the target user is made based on analysis of actual data from other users. As such, the prediction is more accurate.

Specifically, as will be analyzed below, the temporal relationship between dietary habits and health issues can well represent causality thereof. By using such temporal relation, accuracy of the evaluation of a health condition as well as the prediction of health issues can be further improved.

In some example embodiments, reference users matching the target user in terms of dietary habits can be selected so that their data is used to implement personalized evaluation of health conditions of the target user.

Figure 4:
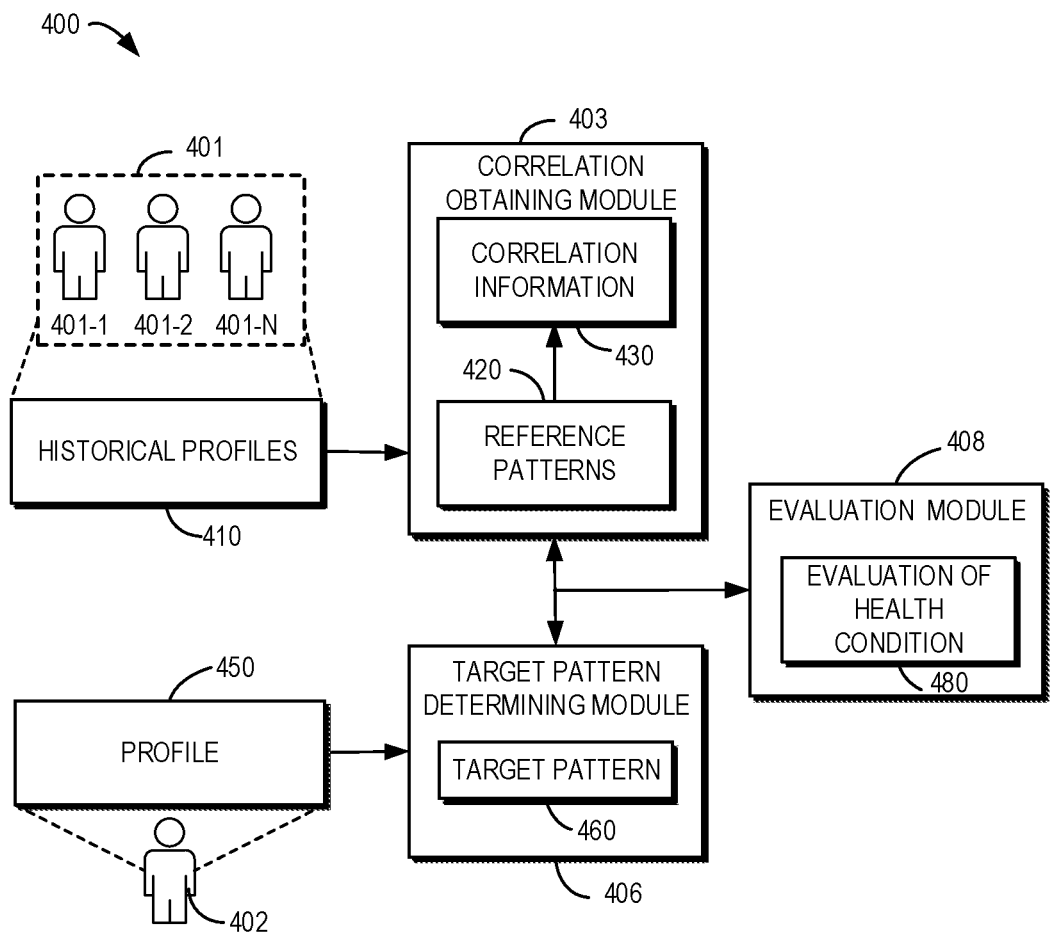
FIG. 4 depicts an exemplary environment in which embodiments of the present disclosure can be implemented.

Referring now to FIG. 4, an exemplary environment 400 in which embodiments of the present disclosure can be implemented is shown. It is to be understood that the structure and elements of the environment 400 are described only for the purpose of illustration without suggesting any limitations as to the scope of the present disclosure.

As shown, in general, the environment 400 includes a correlation obtaining module 403, a target pattern determining module 406 and an evaluation generating module 408. In a nutshell, the correlation obtaining module 403 is configured to obtain the correlation between dietary habits and health issues of reference users 401. The target pattern determining module 406 is configured to determine a target pattern 460 of a target user 402. The evaluation module 408 is configured to generate an evaluation 480 of the health condition of the target user 402. It is to be understood that the reference users 401 and the target user 402 may be any suitable individual person including, but not limited to, a patient.

Now some examples of those modules and the operations/functions thereof will be discussed in detail.

In operation, the correlation obtaining module 403 may obtain historical profiles 410 of multiple reference users 401-1, 401-2 and 401-N (collectively referred to as reference users 401), where N is any suitable natural number greater than two. That is, any suitable number of reference users can be considered.

Each historical profile 410 includes information of at least one dietary habit and at least one health condition of a respective reference user 401. More specifically, the historical profile 410 may indicate at least one dietary habit and at least one health issue of the respective reference user 401. In some implementations, the historical profiles 410 may additionally include any other information of the respective reference users 401 such as gender, age, and so on.

The historical profiles 410 may be collected in any suitable manner. For example, in some implementations, the information on the dietary habits and health conditions of the reference users 401 may be obtained via conversations with the reference users 401. The conversations may be conducted automatically by a computing device and/or manually by human operators. During the conversations, the reference users may be asked to answer questions regarding their dietary habits, heath conditions, health issues, and so on. Alternatively, or in addition, the information of the dietary and health conditions of the reference users 401 may be obtained from questionnaires which are submitted by the reference users 401. The questionnaires may include questions regarding a variety of dietary habits.

It should be noted that any user data collection (e.g., dietary information, health history, biographical information, etc.) is done with user consent via an opt-in and opt-out feature. As known by those skilled in the art, an opt-in and opt-out feature generally relates to methods by which the user can modify a participating status (i.e., accept or reject the data collection). In some embodiments, the opt-in and opt-out feature can include a software application(s) available in, for example, computing devices. Additionally, the user can choose to stop having his/her information being collected or used. In some embodiments, the user can be notified each time data is being collected. The collected data is envisioned to be secured and not shared with anyone without user's consent. The user can stop the data collection at any time.

The correlation obtaining module 403 generates reference patterns 420 for the reference users 401 based on the historical profiles 410. Each reference pattern 420 at least indicates temporal characteristics of at least one dietary habit and at least one health issue of a respective reference user.

For example, the temporal characteristics of dietary habits may include at least one of the following: a time period corresponding to the dietary habit, a time duration of the dietary habit, starting and end time points of the dietary habit, or a time point at which the dietary habit occurs.

Likewise, the temporal characteristics of health issues may include at least one of the following: a time period corresponding to the health issue, a time duration of the health issue, starting and end time points of the health issue, or a time point at which the health issue occurs.

The granularity of the temporal characteristics of the dietary habit and health issues may be of any suitable time scale. For example, the granularity of the time periods may be of any suitable time length, such as weeks, months, years, etc.

Figure 5:
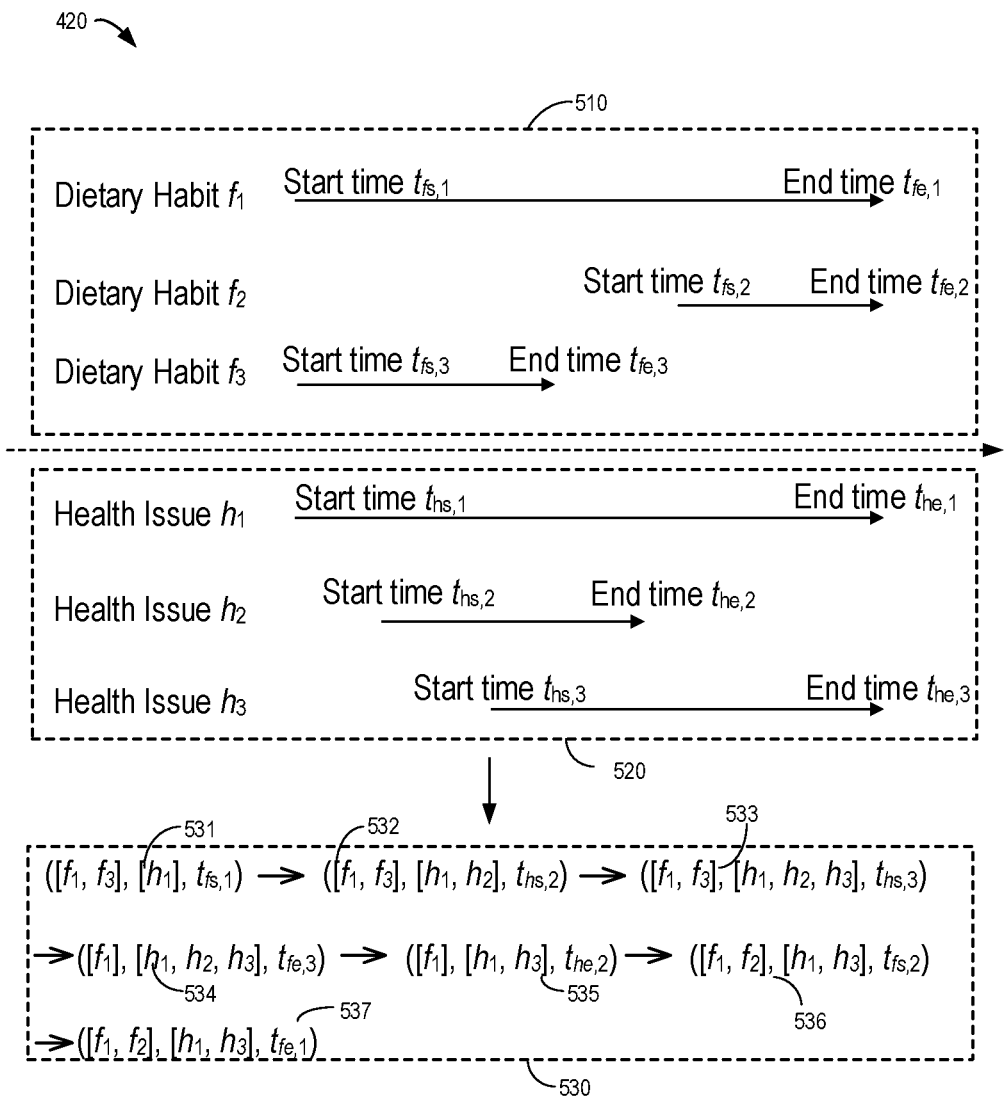
FIG. 5 depicts a schematic diagram of an exemplary reference pattern, according to embodiments of the present disclosure.

Referring now to FIG. 5, a schematic diagram of an example of the reference pattern 420 is shown, according to an embodiment of the present disclosure. As shown in FIG. 5, the reference pattern 420 includes a dietary habit pattern 510 and a health issue pattern 520. The dietary habit pattern 510 may indicate temporal characteristics of dietary habits $f_1$, $f_2$ and $f_3$. For example, the dietary habit $f_1$ starts at "Start time $t_{fs,1}$" and ends at "End time $t_{fe,1}$". Alternatively, or in addition, time periods corresponding to the dietary habits $f_1$, $f_2$ and $f_3$ may be identified in the dietary habit pattern 510. For example, a time period corresponding to the dietary habit $f_1$ may be the first three months of a year. The health issue pattern 520 indicates temporal characteristics of the health issues $h_1$, $h_2$ and $h_3$. For example, the health issue $h_1$ starts at "Start time $t_{hs,1}$" and ends at "End time $t_{he,1}$". Alternatively, or in addition, time periods corresponding to the health issues $h_1$, $h_2$ and $h_3$ may be identified the health issue pattern 520. For example, a time period corresponding to the health issue $h_1$ may be the last two months of a year.

A temporal relation sequence 530 may be generated based on the dietary habit pattern 510 and the health issue pattern 520 if the dietary habit pattern 510 and the health issue pattern 520 are aligned in time. FIG. 5 shows an example format for the temporal relation sequence 530. Each of the elements 531-537 of the temporal relation sequence 530 may represent one or more dietary habits and one or more health issues of the reference user at an instant time. For example, the element 533 may indicate that the reference user has the dietary habits $f_1$ and $f_3$ as well as the health issues $h_1$, $h_2$ and $h_3$ at the instant time $t_{hs,3}$, which is the start time of the health issue $h_3$. The correlation obtaining module 403 (FIG. 4) may use the temporal relation sequence 530 to determine the correlation between dietary habits and health issues of the reference users 401 (FIG. 4).

It is to be understood that the number of dietary habits and health issues shown in FIG. 5 is merely for purpose of illustration. The reference pattern 420 (FIG. 4) may correspond to any suitable number of dietary habits and health issues.

Referring back to FIG. 4, the correlation obtaining module 403 is configured to determine a correlation between the dietary habits and health issues of the reference users 401 based on the reference patterns 420. The correlation between the dietary habits and health issues of the reference users 401 may be also referred to as correlation information 430. The correlation information 430 may associate a dietary habit with a health issue which may be caused by the dietary habit and associate a health issue with a dietary habit which may cause the health issue.

The target pattern determining module 406 is configured to obtain a profile 450 of a target user 402. The profile 450 includes information of at least one dietary condition of the target user 402. More specifically, the profile 450 may indicate at least one dietary habit of the target user 402. In some implementations, the profile 450 may additionally include any other information of the target user 402 such as gender, age, and so on.

Similar to the historical profiles 410, the profile 450 may be collected in any suitable manner. For example, in some implementations, the information of the dietary condition of the target user 402 may be obtained via a conversation with the target user 402. The conversation may be conducted automatically by a computing device and/or manually by human operators. During the conversation, the target user 402 may be asked to answer questions regarding his/her dietary habits. In these implementations, the profile 450 of the target user 402 may be updated during the conversation.

Alternatively, or in addition, the information of the dietary condition of the target user 402 may be obtained from a questionnaire which is submitted by the target user 402. The questionnaire may include questions regarding a variety of dietary habits.

The target pattern determining module 406 may determine a target pattern 460 of the target user 402 at least in part based on the profile 450. For example, the target pattern 460 may be generated based on the information of the dietary condition of the target user 402. In some embodiments, an initial pattern for determining the target pattern 460 may be first generated. The initial pattern may be gradually updated to the target pattern 460 through an interactive conversation with the target user 402.

The target pattern 460 at least indicates temporal characteristics of at least one dietary habit of the target user 402. The temporal characteristics of the target pattern 460 are similar to those described above with respect to the reference pattern 420. The target pattern 460 may include at least a dietary habit pattern similar to the dietary habit pattern 510 shown in FIG. 5. The target pattern 460 may further include a health issue pattern similar to the health issue pattern 520 shown in FIG. 5.

The evaluation module 408 may generate an evaluation 480 of the health condition of the target user 402 at least in part based on the target pattern 460 and the correlation information 430. The evaluation 480 of the health condition may include identified health issue(s) of the target user 402 and potential health issue(s) to which the target user 402 should pay attention. Such potential health issue(s) may be a health issue(s) the target user 402 is currently having but is not aware of. Or, alternatively, the potential health issue(s) may be a high-risk health issue(s) the target user 402 might have in the future.

Figure 6A:
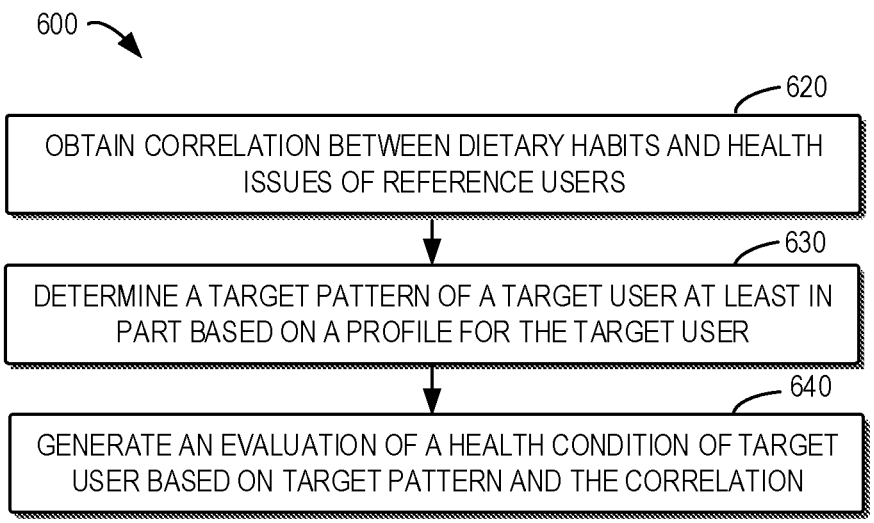
FIG. 6A depicts a flowchart of an exemplary method for evaluation of health issues, according to embodiments of the present disclosure.
Figure 7:
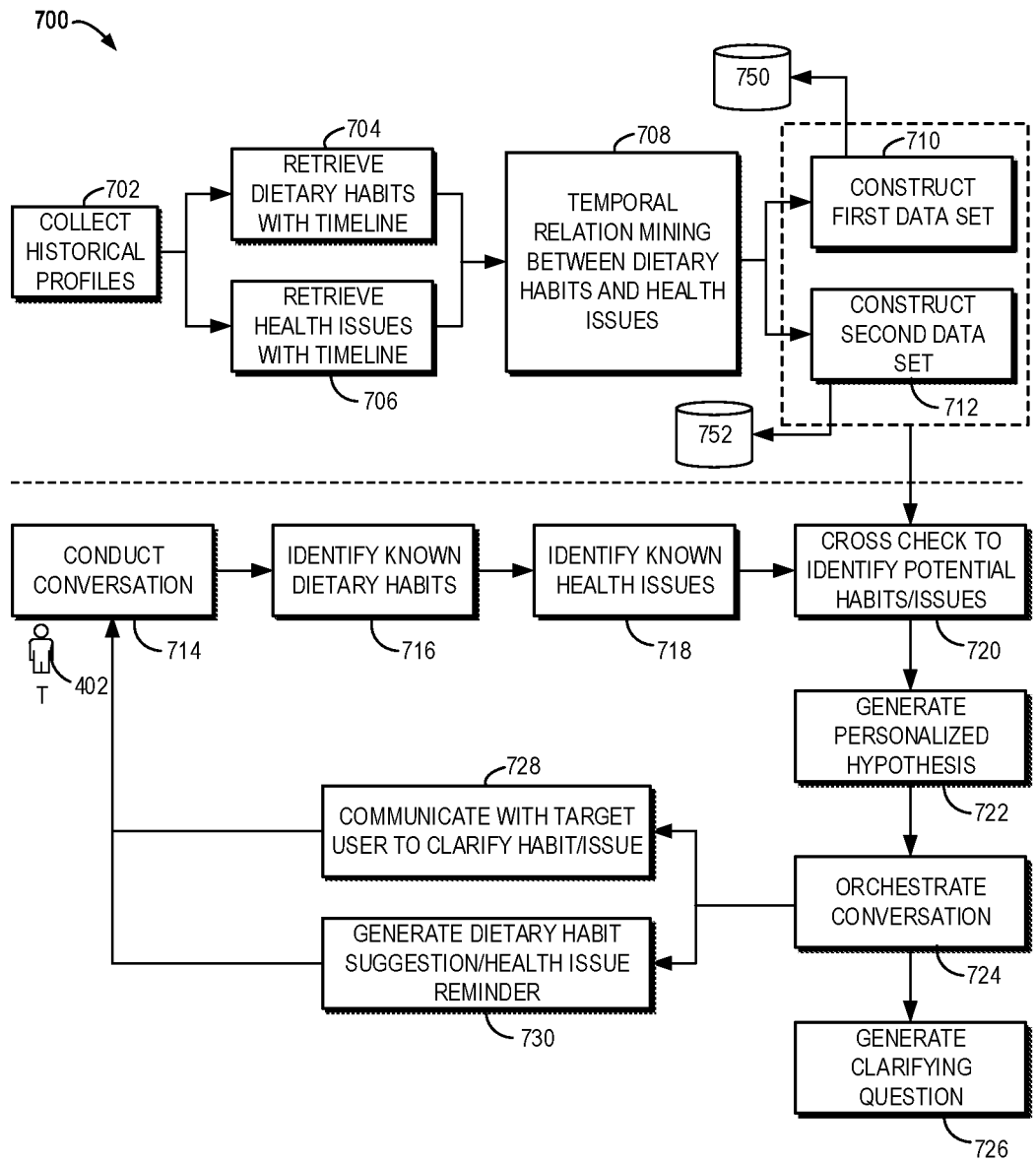
FIG. 7 depicts a schematic diagram of an exemplary process for health issue evaluation, according to an embodiment of the present disclosure.

Referring now to FIG. 6A, a flowchart of an exemplary method 600 for evaluation of health issues is shown, according to an embodiment of the present disclosure. For ease of understanding, the method 600 will be described with reference to FIG. 4 and FIG. 7. FIG. 7 depicts a schematic diagram of an exemplary process 700 for evaluation of health issues according to an embodiment of the present disclosure. It is to be understood that the example process 700 may be considered as a specific implementation of the health issue evaluation method of the present disclosure.

At 620, a correlation between dietary habits and health issues of the reference users 401 can be obtained. The correlation is determined based on the reference patterns 420. For example, the correlation obtaining module 403 may determine the correlation information 430 based on the reference patterns 420. As described above, each reference pattern 420 may indicate temporal characteristics of at least one dietary habit and at least one health issue of a respective reference user. For example, each reference pattern 420 may take the form shown in FIG. 5.

With reference now to FIG. 7, an example process for determining the correlation is illustrated, according to an embodiment of the present disclosure. In the example process 700, at 702, the historical profiles 410 of the reference users 401 may be collected. At 704, for each reference user 401, dietary habits with a timeline may be retrieved from the historical profile 410 of the respective reference user 401. Accordingly, the dietary habit pattern may be generated for the respective reference user 401. At 706, for each reference user 401, health issues with a timeline may be retrieved from the historical profile 410 of the respective reference user 401. Accordingly, the health issue pattern may be generated for the respective reference user 401.

Next, at 708, temporal relation mining between the dietary habits and health issues of the reference user 401 may be performed. To understand the temporal relation mining, concepts of a temporal relation and a support rate is first described. In a reference pattern with a dietary habit X and a health issue Y, if a time period corresponding to the dietary habit X and a time period corresponding to the health issue Y overlap, the dietary habit X and the health issue Y may have the temporal relation. The temporal relation may represent causality between the dietary habit X and the health issue Y.

The correlation (X, Y) may represent that the dietary habit X might cause the health issue Y. The support rate for the correlation (X, Y) may be determined as a ratio of the number of valid (X, Y) cases to the total number of Y cases, where the Y cases may be defined as the reference patterns with the health issue Y, and the valid (X, Y) cases may be defined as the reference patterns in which the dietary habit X and the health issue Y have the temporal relation. Accordingly, the support rate for the correlation (X, Y) can be determined based on the number of reference patterns in which the dietary habit X and the health issue Y have the temporal relation and the total number of the reference patterns have the health issue Y. The support rate for the correlation (X, Y) may represent the possibility that a user with the health issue Y has the dietary habit X.

Likewise, the correlation (Y, X) may represent that the health issue Y might be caused by the dietary habit X. The support rate for the correlation (Y, X) may be determined as a ratio of the number of valid (Y, X) cases to the total number of X cases, where the X cases may be defined as the reference patterns with the dietary habit X, and the valid (Y, X) cases may be defined as the reference patterns in which the dietary habit X and the health issue Y have the temporal relation. Accordingly, the support rate for the correlation (Y, X) can be determined based on the number of the reference patterns in which the dietary habit X and the health issue Y have the temporal relation and the total number of the reference patterns with the dietary habit X. The support rate for the correlation (Y, X) may represent the possibility that a user with the dietary habit X has the health issue Y.

At 710, a first data set 750 for the correlation between the dietary habits and health issues may be constructed based on results of the temporal relation mining. The first data set 750 may include a plurality of data items. Each data item indicates a correlation between a dietary habit and a health issue. Additionally, in some embodiments, the first data set 750 may include reference pattern(s) in which the correlation indicated by each data item is found. The support rate for the correlation exceeds a first threshold. The first threshold may be configured with a relatively large value, for example 0.8, 0.85, 0.9 or the like. If the correlation between the dietary habit X and the health issue Y is indicated in the first data set 750, it indicates that a user with the dietary habit X may be likely to have the health issue Y, or indicates that a user with the health issue Y may be likely to have the dietary habit X.

As an example, the correlation $(X_1, Y_1)$ with a support rate of 0.96 may be indicated in the first data set 750. Accordingly, the health issue $Y_1$ may correspond to the dietary habit $X_1$. In the case where the dietary habit $X_1$ represents an increase preference for salty food and the health issue Y1 represents high blood pressure, it may indicate that 96% of the reference users with high blood pressure may excessively consume salty food. Therefore, the health issue included in the first data set 750 can be considered as being correlated to a definite dietary habit.

At 712, a second data set 752 for the correlation between dietary habits and health issues may be constructed based on the results of the temporal relation mining. The second data set 752 may include a plurality of data items. Each data item indicates a correlation between a dietary habit and a health issue. Additionally, in some embodiments, the second data set 752 may include the reference pattern(s) in which the correlation indicated by each data item is found. The support rate for the correlation is below the first threshold and exceeds a second threshold. The second threshold may be configured with a relatively small value such as, for example, 0.5, 0.4, 0.3 or less.

In an example implementation, the second data set 752 may include a plurality of data items indicating the correlations $(X, Y_1), (X, Y_2), \ldots, (X, Y_n)$, respectively, where n is a natural number. The correlations indicate that a dietary habit X is correlated to a plurality of health issues $Y_1, Y_2, \ldots, Y_n$. This means that a user with the dietary habit X may have one or more of the plurality of health issues $Y_1, Y_2, \ldots, Y_n$. Alternatively, or in addition, the second data set 752 may include a plurality of data items indicating the correlations $(Y, X_1), (Y, X_2), \ldots, (Y, Xm)$, respectively, where m is a natural number. The correlations indicate that a health issue Y is correlated to a plurality of dietary habits $X_1, X_2, \ldots, X_m$. This means that a user with the health issue Y may have one or more of the plurality of dietary habits $X_1, X_2, \ldots, X_m$.

As an example, in the case that the first threshold is 0.8 and the second threshold is 0.3, the support rates for the correlations indicated in the second data set 752 are between 0.3 and 0.8. For example, if the support rate for the correlation (X, Y) is 0.35, this means that the possibility of a user with health issue Y having dietary habit X is 35%.

It is to be understood that the above values for support rates and thresholds are described merely for illustration purpose without suggesting any limitations as to the scope. Likewise, the constructions of the first and second data sets may be in any suitable formats. Also, the correlation between the health issues and dietary habits of the reference users can be maintained in any suitable manners.

The correlation between the dietary habits and health issues of the reference users 401 may be determined as described above. Referring back to FIG. 6A, at 630, the target pattern 460 of the target user 402 is determined at least in part based on a profile 450 of the target user 402. The target pattern 460 at least indicates a temporal characteristic of at least one dietary habit of the target user 402. For example, the target pattern 460 may at least include the dietary habit pattern of the target user 402. Or, alternatively, the target pattern 460 may include both the dietary habit pattern and the health issue pattern.

In some embodiments, the target pattern 460 may be determined only based on the profile 450. For example, the target user 402 may submit a questionnaire which includes information regarding a variety of dietary habits (and optionally a variety of health issues). Then, the target pattern 460 may be determined based on the information in the questionnaire.

Figure 6B:
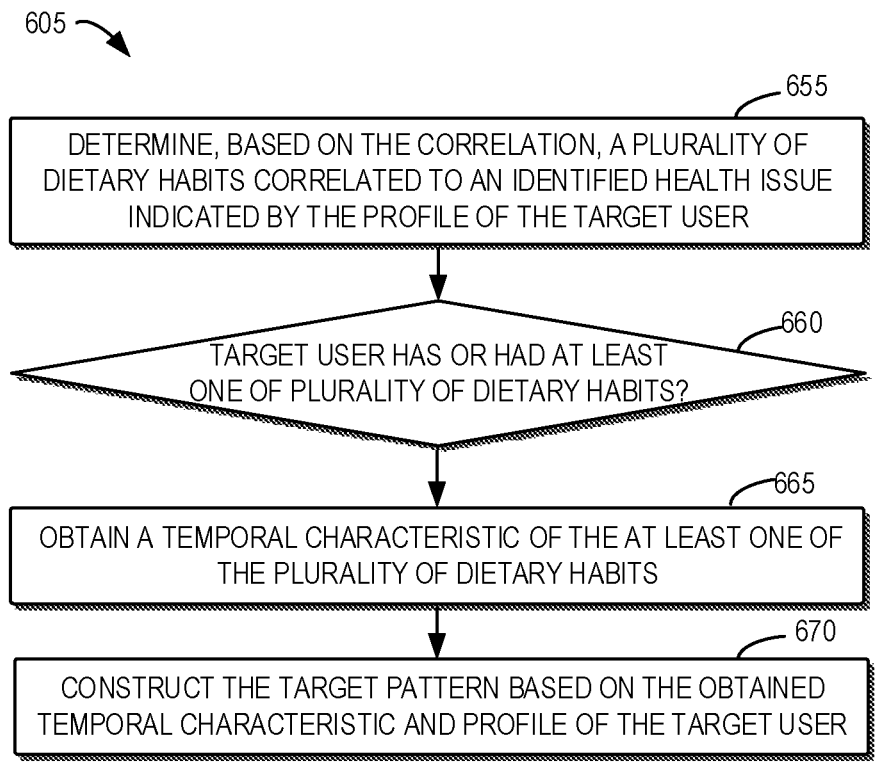
FIG. 6B depicts a flowchart of an exemplary method for determining target pattern, according to embodiments of the present disclosure.

In some embodiments, the target pattern 460 may be determined further based on the correlation information 430. FIG. 6B illustrates an example of such embodiments. FIG. 6B depicts a flowchart of an example method 605 for determining target pattern, according to embodiments of the present disclosure. The method 605 may be implemented by the target pattern determining module 406 as shown in FIG. 4, and may be an implementation of the block 630. The profile 450 of the target user 402 may indicate an identified health issue of the target user 402. For example, the identified health issue may be provided by the target user 402 during an interactive conversation with the target user 402.

At 655, a plurality of dietary habits correlated to the identified health issue may be determined based on the correlation between health issues and dietary habits of the reference users 401. For example, the target pattern determining module 406 may search the first data set 750 and the second data set 752 for the identified health issue. If the identified health issue is indicated in the second data set 752 for example, the plurality of dietary habits (which may be referred to as "correlated dietary habits") correlated to the identified health issue can be determined from the second data set 752. In this case, the identified health issue of the target user 402 may be caused by any of the plurality of correlated dietary habits. Therefore, it may need to check whether the target user 402 has any of the plurality of correlated dietary habits.

At 660, the target pattern determining module 406 may determine whether the target user 402 has or had at least one of the plurality of correlated dietary habits. For example, during the interactive conversation, a question regarding whether the target user 402 has or had at least one of the plurality of correlated dietary habits may be provided to the target user 402 and an answer may be received accordingly from the target user 402. In some embodiments, before checking whether the target user 402 has or had at least one of the plurality of correlated dietary habits, a reference user matching with the target user 402 may be selected. In order to select the reference user matching the target user 402, the reference pattern(s) with the identified health issue may be first determined and a health issue similarity may be calculated similarly, as will be described below with reference to FIG. 8. The target pattern determining module 406 may only check the correlated dietary habit which is indicated by the reference pattern of the selected reference user. The correlated dietary habit which is not indicated by the reference pattern of the selected reference user may not be checked.

If at 660, it is determined that the target user 402 has or had at least one of the plurality of correlated dietary habits, the method proceeds to 665. At 665, temporal characteristics of the at least one of the plurality of correlated dietary habits may be obtained. For example, a further question regarding the time period corresponding to the at least one correlated dietary habit may be provided to the target user 402 and an answer may accordingly be received from the target user 402. Then, at 670, the target pattern 460 may be constructed based on the obtained temporal characteristics and the profile of the target user 402. The target pattern 460 may at least indicate the temporal characteristics of the at least one correlated dietary habits of the target user 402.

In some embodiments, the method 605 may include additional steps to add a temporal characteristic of a further identified health issue to the target pattern 460. The profile 450 of the target user 402 may indicate an identified dietary habit of the target user 402. For example, the identified dietary habit may be provided by the target user 402 during the interactive conversation. Then, the target pattern determining module 406 may determine the health issue(s) correlated to the identified dietary habit based on the correlation between the health issues and dietary habits of the reference users 401. If the identified dietary habit corresponds to a particular health issue, the target pattern determining module 406 may further determine whether the target user 402 has or had the particular health issue. If the target user 402 has or had the particular health issue, a temporal characteristic of the particular health issue may be added to the target pattern 460. For example, the first data set 750 and the second data set 752 may be searched for the identified dietary habit. If the identified dietary habit is indicated in the first data set 750 for example, the particular health issue corresponding to the identified dietary habit can be determined from the first data set 750. Then, a question regarding whether the target user 402 has or had the particular health issue may be provided to the target user 402 and an answer may be received from the target user 402 accordingly.

With continued reference to FIG. 7, an example process is described in which the target pattern 460 may be constructed as described above with reference to FIG. 6B, according to an embodiment of the present disclosure. As mentioned above, in some implementations, the profile 450 may be obtained via the interactive conversation with the target user 402. At 714, an interactive conversation may be conducted with the target user 402, for example, automatically by a computing device. At 716, one or more known dietary habits of the target user 402 may be identified via the conversation. In addition, at 718, one or more known health issues of the target user 402 may be identified via the conversation. Accordingly, an initial pattern of the target user 402 may be constructed based on the identified dietary habit(s) and optionally the identified health issue(s).

At 720, cross check may be performed to identify other dietary habit(s) and/or health issue(s) of the target user 402. The dietary habits correlated to the identified health issue (e.g., identified at 718) may be determined. For example, the first data set 750 and the second data set 752 may be searched for the identified health issue. For example, if the identified health issue is indicated in the second data set 752, the dietary habits correlated to the identified health issue may be determined from the second data set 752. For purpose of discussion, it is assumed that the second data set 752 indicates that the identified health issue is correlated to three dietary habits L, M and N.

If at least one of the three dietary habits L, M and N is not included in the already identified dietary habits (e.g., identified at 716), a clarifying question regarding the dietary habits L, M and N may be generated at 726. The clarifying question may ask the target user 402 to confirm whether he/she have the three dietary habits L, M and N during certain time periods. At 724, the conversation is orchestrated, for example, by a conversation orchestrator. At 728, communication with the target user 402 may be performed to clarify the correlated dietary habits. Then, at 716, one or more of the dietary habits L, M and N may be identified based on the answer from the target user 402. In this way, the initial pattern can be updated by adding the temporal characteristics (e.g., the time periods) of the newly identified one or more dietary habits. Similar process may be applied to clarify the health issues of the target user 402.

The embodiments where the target pattern 460 can be determined based on the correlation are described above with reference to FIG. 6B. Now referring back to FIG. 6A, at 640, an evaluation of a health condition of the target user 402 is generated based on the target pattern 460 and the correlation. In addition to the health issues which are already identified (e.g., the health issues given by the target user 402 during the conversation), the evaluation of the health condition may include current or potential health issue(s) that the target user 402 may develop in the future. For example, if the target pattern 460 indicates that the target user 402 has a dietary habit Q for a long time, and the dietary habit Q is correlated to a health issue P (e.g., as indicated in the first data set 750), then it may be determined that the target user 402 may be very likely to develop the health issue P. Accordingly, the health issue P may be identified as a potential issue for the target user 402.

In some embodiments, the evaluation of the health condition of the target user 402 may further be generated based on the reference pattern 420 of the reference user 401 which matches the target user 402 in term of dietary habit. In such embodiments, at least one reference user may be selected from the plurality of reference users 401 so that a dietary habit similarity between the target user 402 and the selected at least one reference user 401 exceeds a threshold. For purpose of discussion, the selected at least one reference user may be referred to as the matching reference user herein.

Figure 8:
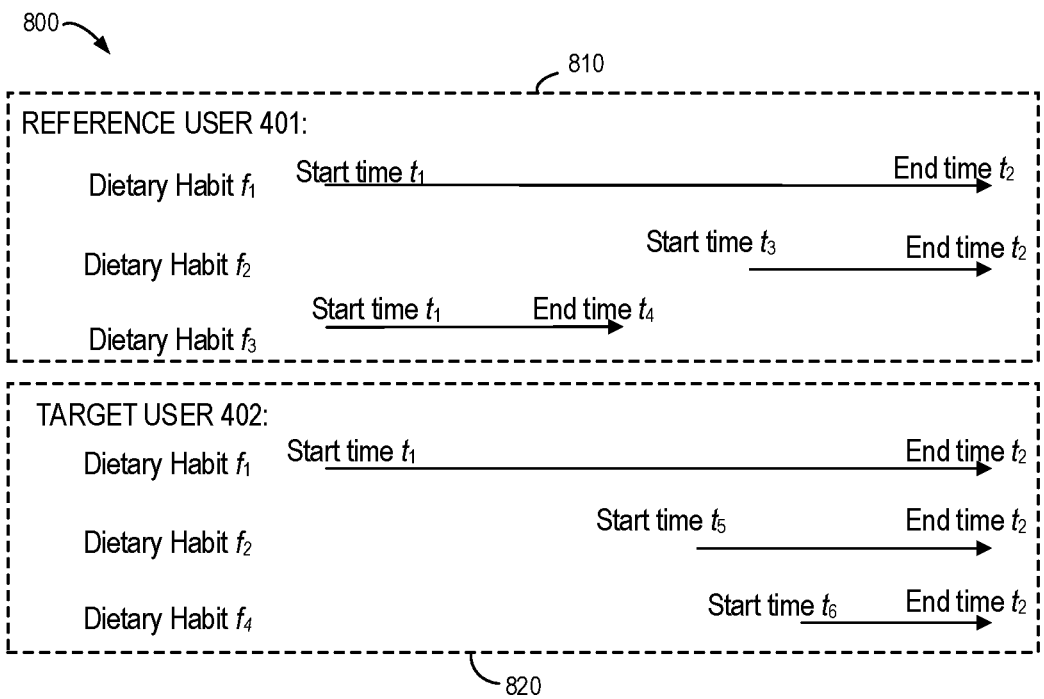
FIG. 8 depicts a schematic diagram of comparison between two dietary habit patterns, according to embodiments of the present disclosure.

Referring now to FIG. 8, a selection of at least one reference user matching the target user 402 is illustrated, according to an embodiment of the present disclosure. Specifically, FIG. 8 depicts a schematic diagram 800 of comparison between two dietary habit patterns 810 and 820, according to embodiments of the present disclosure. In this example, the dietary habit pattern 810 may be a dietary habit part of the reference pattern 420 of the reference user 401. The dietary habit pattern 820 may be a dietary habit part of the target pattern 460 of the target user 402.

The dietary habit similarity between the reference user 401 and the target user 402 may be determined based on an overlapping degree between time periods of at least one dietary habit common to the dietary habit patterns 810 and 820. For the example shown in FIG. 8, the dietary habit similarity between the reference user 401 and the target user 402 may be calculated as (1.0+0.8+0.0+0.0)/4=0.45, where the similarity values for the dietary habits $f_1$, $f_2$, $f_3$, $f_4$ are 1.0, 0.8, 0.0 and 0.0, respectively and may be determined based on an overlapping degree of time periods. Specifically, for the dietary habit $f_1$ common to the dietary habit patterns 810 and 820, a ratio of the length of the time period (from "Start time $t_1$" to "End time $t_2$") indicated by the dietary habit patterns 810 to the length of the time period (from "Start time $t_1$" to "End time $t_2$") indicated by dietary habit patterns 820 is 1.0, and can be determined as the similarity value for the dietary habits $f_1$.

The similarity value for the dietary habits $f_1$ may represent the contribution of the common dietary habit $f_1$ to the dietary habit similarity. For the dietary habit $f_2$ common to the dietary habit patterns 810 and 820, a ratio of the length of the time period (from "Start time $t_3$" to "End time $t_2$") indicated by the dietary habit patterns 810 to the length of the time period (from "Start time $t_5$" to "End time $t_2$") indicated by dietary habit patterns 820 is 0.8 and can be determined as the similarity value for the dietary habits $f_2$. The similarity value for the dietary habits $f_2$ may represent the contribution of the common dietary habit $f_2$ to the dietary habit similarity. Since the dietary habits $f_3$, $f_4$ are not common to the dietary habit patterns 810 and 820, the similarity values for the non-common dietary habits $f_3$, $f_4$ are both 0. The non-common dietary habits $f_3$, $f_4$ have no contribution to the dietary habit similarity. It is to be understood that the overlapping of time periods may be considered in the relative time scale rather than the absolute time scale. In order to determine the dietary habit similarity, the dietary habit patterns 810 and 820 may be first aligned to each other in time.

If the dietary habit similarity exceeds the threshold, the reference user 401 may be considered as the matching reference user of the target user 402 in terms of dietary habit. In some embodiments, dietary habit similarities for all the reference users 401 may be calculated to find out all the matching reference users. This process may be referred to as a fine-grained search based on a temporal relation.

In some embodiments, if the target pattern 460 additionally includes a health issue pattern, a health issue similarity may be determined similarly based on the health issue patterns of the target user 402 and the reference user 401. Thus, the determination of the health issue similarity is not repeated here.

Once the matching reference user (e.g., the reference user 401-1) is selected, a potential health issue of the target user 402 may be identified based on the health issues indicated by the reference pattern 420 of the matching reference user 401-1 and the correlation. In some embodiments, the health issue indicated by the health issue pattern of the matching reference user 401-1 but not indicated by the health issue pattern of the target user 402 may be determined as a potential health issue of the target user 402.

In some embodiments, the potential issue(s) of the target user 402 may also be identified based on the correlation information 430. The evaluation module 408 may determine a dietary habit (which may be referred to as a correlated dietary habit) correlated to the at least one health issue which is indicated by the reference pattern 420 of the matching reference user 401-1 based on the correlation between the dietary habits and health issues of the reference users 401. For example, the correlated dietary habit may be determined from the first data set 750 or the second data set 752 as shown in FIG. 7.

If the correlated dietary habit is also indicated by the target pattern 460 of the target user 402 or, stated differently, if the target user 402 also has or had the correlated dietary habit, then the health issue indicated by the reference pattern 420 of the matching reference user 401-1 may be identified as the potential issue of the target user 402. If more than one matching reference user is selected, other potential issues may be identified similarly.

In such embodiments, the selection of those reference users matching the target user in terms of dietary habit is a fine-grain search process. In this way, their data can be used to implement personalized evaluation of health conditions of the target user.

In some embodiments, a dietary habit suggestion for the target user 402 may further be generated based on the reference pattern of the matching reference user 401-1 and the correlation information 430. For example, if a certain dietary habit of the matching reference user 401-1 is correlated to a health issue which is not indicated by the target pattern 460, the generated suggestion may suggest the target user 402 to avoid that dietary habit.

In some embodiments, a health issue reminder may further be generated and provided to the target user 402. If the evaluation of the health condition of the target user 402 indicates that the target user 402 may have a potential health issue, the generated reminder may remind the target user 402 to pay attention to the potential health issue. For example, the generated reminder may remind the target user 402 of a physical examination related to the potential health issue. For example, referring to the example process 700, at 730, the dietary habit suggestion and/or health issue reminder may be provided to the target user 402 via the interactive conversation.

According to embodiments of the present invention as described above, the health condition of the target user can be evaluated based on the collected dietary habits of the target user. In making the evaluation, the correlation between dietary habits and health issues is also taken into account and such correlation is determined based on the dietary habits and health issues of multiple reference users. In this way, the prediction directed to the target user is made based on analysis of actual data from other users. As such, the prediction is more accurate.

It should be noted that the health condition evaluation according to embodiments of this disclosure could be implemented by computer system/server 12 of FIG. 1.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
   using a collection of historical profiles associated with multiple reference users, generating, by one or more processors, correlations between dietary habits and health issues of the multiple reference users, each of the correlations being determined based on a respective temporal relation sequence of a respective reference pattern associated with a respective reference user of the multiple reference users, each of the reference patterns indicating temporal characteristics of multiple dietary habits and at least one health issue of the respective reference user of the multiple reference users, the temporal relation sequence indicating a dietary habit of the multiple dietary habits and the at least one health issue of the respective reference user were aligned in time by occurring at least partially simultaneously;
   determining, by the one or more processors, a target pattern of a target user at least in part based on a profile of the target user, the target pattern at least indicating temporal characteristics of multiple dietary habits of the target user;
   generating, by the one or more processors, an evaluation of a health condition of the target user based on the target pattern and the correlations and based on the target pattern having a similarity to a reference pattern of at least one of the reference users that exceeds a predetermined threshold value, the similarity being determined based on the multiple dietary habits being weighted based on a ratio of the overlap of their respective time period of occurrence compared to corresponding time period of occurrence for corresponding dietary habits of the reference users, the overlap being determined for a relative time scale, wherein the evaluation is further based on a first correlation from the at least one of the reference users; and
   sending, by the one or more processors, a dietary habit suggestion and a health issue notification to a target user device based on the evaluation of the health condition of the target user, wherein the health issue notification indicates a potential health issue for the target user and a recommended physical examination that relates to the potential health issue.

2. The computer-implemented method of claim 1, wherein the temporal characteristics of the multiple dietary habits of the respective reference user comprise a respective time period corresponding to the respective dietary habit of the respective reference user,
   wherein the temporal characteristics of the at least one health issue of the respective reference user comprise a time period corresponding to the at least one health issue of the respective reference user, and
   wherein the temporal characteristics of the multiple dietary habits of the target user comprise a respective time period corresponding to the respective dietary habit of the target user.

3. The computer-implemented method of claim 1, wherein the profile of the target user further indicates a health condition of the target user, and wherein the target pattern is further determined via:
   determining, by the one or more processors and based on the correlations, that at least some of the multiple dietary habits of the multiple reference users are correlated to the health condition of the target user;
   obtaining, by the one or more processors, temporal characteristics of the at least some of the multiple dietary habits of the multiple reference users; and
   constructing, by the one or more processors and before the evaluation of the health condition is generated, the target pattern further based on the obtained temporal characteristics and the correlated at least some of the multiple dietary habits of the multiple reference users.

4. The computer-implemented method of claim 1, further comprising:
   comparing, by the one or more processors, the multiple dietary habits of the target user to the multiple dietary habits in the collection of the historical profiles so that the potential health issue for the target user is identified from the collection of the historical profiles, the identifying being based on matches of one or more of the multiple dietary habits of the target user to one or more of the dietary habits of the multiple reference users;
   generating, via the one or more processors, one or more automated questions for the target user regarding the identified potential health issues to inquire whether the target user has or had the identified potential health issue; and in response to a determination that the target user has or had the identified potential health issue, adding via the one or more processors temporal characteristics of the identified potential health issue to the target pattern before the evaluation of the health condition is generated.

5. The computer-implemented method of claim 4, further comprising:

in further response to the determination that the target user has or had the identified potential health issue, generating, via the one or more processors, one or more automated questions for the target user regarding the temporal characteristics of the identified potential health issue; and wherein in response to receiving a target user response to the one or more automated questions for the target user regarding the temporal characteristics of the identified potential health issue, the adding of the temporal characteristics to the target pattern is performed based on the target user response.

6. The computer-implemented method of claim 1, wherein the potential health issue is identified from the at least one of the reference users whose reference pattern had the similarity to the target pattern that exceeded the predetermined threshold value.

7. A system comprising:
one or more processors;
a memory coupled to the one or more processors; and
computer-readable instructions stored in the memory, the instructions, when executed by the one or more processors, causing the one or more processors to perform a method comprising:

using a collection of historical profiles associated with multiple reference users, generating correlations between dietary habits and health issues of the multiple reference users, each of the correlations being determined based on a respective temporal relation sequence of respective reference patterns associated with a respective reference user of the multiple reference users, each of the reference patterns indicating temporal characteristics of multiple dietary habits and at least one health issue of the respective reference user of the multiple reference users, the temporal relation sequence indicating a dietary habit of the multiple dietary habits and the at least one health issue of the respective reference user were aligned in time by occurring at least partially simultaneously;

determining a target pattern of a target user at least in part based on a profile of the target user, the target pattern at least indicating temporal characteristics of multiple dietary habits of the target user;

generating an evaluation of a health condition of the target user based on the target pattern and the correlations and based on the target pattern having a similarity to a reference pattern of at least one of the reference users that exceeds a predetermined threshold value, the similarity being determined based on the multiple dietary habits being weighted based on a ratio of the overlap of their respective time period of occurrence compared to corresponding time period of occurrence for corresponding dietary habits of the reference users, the overlap being determined for a relative time scale, wherein the evaluation is further based on a first correlation from the at least one of the reference users; and sending a dietary habit suggestion and a health issue notification to a target user device based on the evaluation of the health condition of the target user, wherein the health issue notification indicates a potential health issue for the target user and a recommended physical examination that relates to the potential health issue.

8. The system of claim 7, wherein the temporal characteristics of the multiple dietary habits of the respective reference user comprise a respective time period corresponding to the respective dietary habit of the respective reference user, wherein the temporal characteristics of the at least one health issue of the respective reference user comprise a time period corresponding to the at least one health issue of the respective reference user, and wherein the temporal characteristics of the multiple dietary habits of the target user comprise a respective time period corresponding to the respective dietary habit of the target user.

9. The system of claim 7, wherein the profile of the target user further indicates a health condition of the target user, and wherein the target pattern is further determined via:

determining, based on the correlations, that at least some of the multiple dietary habits of the multiple reference users are correlated to the health condition of the target user;

obtaining temporal characteristics of the at least some of the multiple dietary habits of the multiple reference users; and constructing, before the evaluation of the health condition is generated, the target pattern further based on the obtained temporal characteristics and the correlated at least some of the multiple dietary habits of the multiple reference users.

10. The system of claim 7, wherein the method further comprises:

comparing the multiple dietary habits of the target user to the multiple dietary habits in the collection of the historical profiles so that the potential health issue for the target user is identified from the collection of the historical profiles, the identifying being based on matches of one or more of the multiple dietary habits of the target user to one or more of the dietary habits of the multiple reference users;

generating one or more automated questions for the target user regarding the identified potential health issue to inquire whether the target user has or had the identified potential health issue; and in response to a determination that the target user has or had the identified potential health issue, adding temporal characteristics of the identified potential health issue to the target pattern before the evaluation of the health condition is generated.

11. The system of claim 7, wherein the potential health issue is identified from the at least one of the reference users whose reference pattern had the similarity to the target pattern that exceeded the predetermined threshold value.

12. A computer program product comprising:
one or more non-transitory computer readable storage media, and program instructions collectively stored on the one or more non-transitory computer readable storage media, the program instructions comprising:

using a collection of historical profiles associated with multiple reference users, program instructions to generate correlations between dietary habits and health issues of the multiple reference users, each of the correlations being determined based on a respective temporal relation sequence of a respective reference pattern associated with a respective reference user of the multiple reference users, each of the reference patterns indicating temporal characteristics of multiple dietary habits and at least one health issue of the respective reference user of the multiple reference users, the temporal relation sequence indicating a dietary habit of the multiple dietary habits and the at least one health issue of the respective reference user are aligned in time by occurring at least partially simultaneously;

program instructions to determine a target pattern of a target user at least in part based on a profile of the target user, the target pattern at least indicating temporal characteristics of multiple dietary habits of the target user;

program instructions to generate an evaluation of a health condition of the target user based on the target pattern and the correlations and based on the target pattern having a similarity to a reference pattern of at least one of the reference users that exceeds a predetermined threshold value, the similarity being determined based on the multiple dietary habits being weighted based on a ratio of the overlap of their respective time period of occurrence compared to corresponding time period of occurrence for corresponding dietary habits of the reference users, the overlap being determined for a relative time scale, wherein the evaluation is further based on a first correlation from the at least one of the reference users; and program instructions to send a dietary habit suggestion and a health issue notification to a target user device based on the evaluation of the health condition of the target user, wherein the health issue notification indicates a potential health issue for the target user and a recommended physical examination that relates to the potential health issue.

13. The computer program product of claim 12, wherein the temporal characteristics of the multiple dietary habits of the respective reference user comprise a respective time period corresponding to the respective dietary habit of the respective reference user, wherein the temporal characteristics of the at least one health issue of the respective reference user comprise a time period corresponding to the at least one health issue of the respective reference user, and wherein the temporal characteristics of the multiple dietary habits of the target user comprise a respective time period corresponding to the respective dietary habit of the target user.

14. The computer program product of claim 12, wherein the profile of the target user further indicates a health condition of the target user, and wherein the target pattern is further determined via:

determining, based on the correlations, that at least some of the multiple dietary habits of the multiple reference users are correlated to the health condition of the target user;

obtaining temporal characteristics of the at least some of the multiple dietary habits of the multiple reference users; and constructing, before the evaluation of the health condition is generated, the target pattern further based on the obtained temporal characteristics and the correlated at least some of the multiple dietary habits of the multiple reference users.

15. The computer program product of claim 12, wherein the program instructions further comprise:

program instructions to compare the multiple dietary habits of the target user to the multiple dietary habits in the collection of the historical profiles so that the potential health issue for the target user is identified from the collection of the historical profiles, the identifying being based on matches of one or more of the multiple dietary habits of the target user to one or more of the dietary habits of the multiple reference users;

program instructions to generate one or more automated questions for the target user regarding the identified potential health issue to inquire whether the target user has or had the identified potential health issue; and in response to a determination that the target user has or had the identified potential health issue, adding temporal characteristics of the identified potential health issue to the target pattern before the evaluation of the health condition is generated.

16. The computer program product of claim 15, wherein the program instructions further comprise:

in further response to the determination that the target user has or had the identified potential health issue, program instructions to generate one or more automated questions for the target user regarding the temporal characteristics of the identified potential health issue; and wherein in response to receiving a target user response to the one or more automated questions for the target user regarding the temporal characteristics of the identified potential health issue, the adding of the temporal characteristics to the target pattern is performed based on the target user response.

17. The computer program product of claim 12, wherein the potential health issue is identified from the at least one of the reference users whose reference pattern had the similarity to the target pattern that exceeded the predetermined threshold value.

* * * * *